United States Patent [19]

Rhame, Jr.

[11] Patent Number: 5,180,360
[45] Date of Patent: Jan. 19, 1993

[54] ATRAUMATIC EYE PATCH

[76] Inventor: Robert W. Rhame, Jr., P.O. Box 1029, Holly Hill, S.C. 29059

[21] Appl. No.: 685,837

[22] Filed: Apr. 15, 1991

[51] Int. Cl.$^5$ ............................................. A61F 13/12
[52] U.S. Cl. ......................... 602/74; 606/204.25; 602/53; 2/15
[58] Field of Search ............... 128/155, 156, 163, 858, 128/888; 604/294; 2/15; 602/53, 58, 74; 606/204.15, 204.25, 204.35

[56] References Cited

U.S. PATENT DOCUMENTS

| | | |
|---|---|---|
| 655,206 | 8/1900 | Davidson . |
| 2,560,712 | 7/1951 | Bell . |
| 2,891,252 | 6/1959 | Lazo ................................. 2/15 |
| 3,039,459 | 6/1962 | Scholl . |
| 3,092,103 | 6/1963 | Mower . |
| 3,171,410 | 3/1965 | Towle, Jr. et al. . |
| 3,366,112 | 1/1968 | Antonik . |
| 3,490,448 | 1/1970 | Grubb ................................ 602/53 |
| 3,814,095 | 6/1974 | Lubens . |
| 3,908,645 | 9/1975 | Sandvig ........................... 128/156 |
| 4,022,203 | 5/1977 | Ackley . |
| 4,134,401 | 1/1979 | Galician . |
| 4,212,296 | 7/1980 | Schaar . |
| 4,224,945 | 9/1980 | Cohen . |
| 4,377,159 | 3/1983 | Hansen ............................. 602/53 |
| 4,826,009 | 5/1989 | Young .............................. 206/441 |
| 4,995,114 | 2/1991 | Price, Jr. ......................... 128/858 |

Primary Examiner—Paul Prebilic
Attorney, Agent, or Firm—Dority & Manning

[57] ABSTRACT

A self-adhering eye patch with an adhesive backing for securing the patch to the face of a user. The patch includes an inner foam or inflatable bladder for atraumatically maintaining the lid of the eye closed. A cover covers the inner member and the inner member is of sufficient thickness to maintain the lid securely closed without damaging the eye.

11 Claims, 3 Drawing Sheets

ATRAUMATIC EYE PATCH

BACKGROUND OF THE INVENTION

The present invention relates generally to patches for covering eyes and the like, and more particularly to a novel atraumatic eye patch for immobilizing the eyelid.

To fully appreciate the improvement of the present invention, a brief description of the human eye is helpful. The human eye is essentially a non-distensible, fluid filled sac that is divided into two compartments separated by the lens of the eye. The first compartment contains the anterior and posterior chambers which are filled with aqueous humor, and the second compartment is the vitreous chamber which is filled with a gel-like vitreous humor.

The eye and its structures require blood flow and oxygenation. To achieve this, blood is carried to the inner lining of the back of the eyeball, the retina, on which light is received and visual signals developed that are sent to the brain to enable one to see.

Blood is brought into the eye through an artery and a vein in the center of the back of the eye. It is distributed to the various structures in the eye through a series of smaller arteries and veins. The arteries carry blood to structures within the eye and the veins carry blood away from those structures in the eye which run across the back of the eye or retina. These vessels are essentially open or uncovered and exposed to the gel filling the inner compartment of the back of the eye known as the vitreous humor.

Increases in pressure within the eye that are transmitted through the gel to the vessels on the back of the eye can result in the occlusion of these vessels, and thus, the obstruction of blood flow either to or away from the eye. If this persists, loss of vision may result. Pressure applied to the exterior of the eye can be transmitted to this gel, and therefore, to the inside of the eye and may occlude the vessels in the eye. The pressure required to occlude blood flow in these veins or arteries may vary from person to person. In some older persons, very low pressures are all that is required to produce this change.

Numerous diseases or conditions necessitate the patching of one's eye. Such conditions include corneal abrasions, burns (such as welding flash-burns), lacerations and surgery. In addition, conditions such as amblyopia (often called "lazy eye"), lag ophthalmos (poor lid closure frequently seen with thyroid disease and facial nerve palsies), and Corneal Basement Membrane Disease (cornea separation from its underlying support structure or basement membrane) often necessitate patching of the eye.

Excessive pressure applied to the eye by a patch or otherwise can cause numerous problems. For example, with regard to corneal injuries, the corneal epithelium heals denuded areas, such as abrasions, by the horizontal sliding of epithelial cells into the area to cover the defect. Larger defects are filled by a combination of sliding and cell division. The endothelium is the inner layer of cells of the cornea. Extreme elevations of pressure within the eye interfere with the function of the endothelial cells and may produce corneal edema, central retinal artery and vein occlusions or blockages of the arteries and veins that line the back of the eye. In addition, increases in intra-ocular pressure may result in glaucoma and optic nerve damage. Further, unequal focal forces applied to the surface of the globe may cause the retina to tear away from its underlying support structures, thus causing a condition called retinal detachment. This could also cause a detachment of the gel from the surface of the retina, i.e., a vitreous detachment.

The most common currently used method of patching the eye is the use of textile pads which are applied using strips of adhesive tape in various fashions to secure the lid. This is a time consuming process that is sometimes inadequate to maintain closure of the lid and which often results in uncomfortable and excessive pressure on the eye itself.

In addition to the above noted manner of patching an eye, numerous other eye covering devices are known. For example, U.S. Pat. No. 4,677,974 to Leonardi discloses a pirate-type eyelid splint that includes a foam pad mounted on an interior face of a backing. The backing is connected to stretchable straps with velcro ends for adjusting the strap on the head. U.S. Pat. No. 4,134,401 to Galician also discloses an eye patch designed to maintain the lid closed. Galician requires a strip for maintaining the lid closed. U.S. Pat. No. 4,951,658 to Morgan discloses an eye patch with a hydrocolloidal adhesive for adhering to the face of the user. U.S. Pat. No. 4,635,625 to Teeple discloses a surgical eye mask for use during eye surgery. In addition, U.S. Pat. No. 3,092,103 to Mower discloses an adhesive eye patch. Mower is designed to allow the lid to open when the patch is in place.

In addition, bandages of various types are known that incorporate some type resilient member. Examples of these are U.S. Pat. No. 3,366,112 to Antonik, U.S. Pat. No. 4,212,296 to Schaar, U.S. Pat. No. 4,726,364 to Wylan, U.S. Pat. No. 4,972,829 to Kerr, U.S. Pat. No. 655,206 to Davidson, U.S. Pat. No. 3,814,095 to Lubens, U.S. Pat. No. 4,224,945 to Cohen, U.S. Pat. No. 3,039,459 to Scholl, U.S. Pat. No. 3,171,410 to Towle, Jr., U.S. Pat. No. 2,560,712 to Bell, and U.S. Pat. No. 4,022,203 to Ackley.

Therefore, it can be seen that various methods and apparatuses have been provided for covering the eye. However, functional shortcomings of these devices are numerous. For example, many of the prior art devices are difficult to apply, interfere with the wearing of glasses, provide excessive pressure on the eye, or are otherwise unsatisfactory.

SUMMARY OF THE INVENTION

The present invention recognizes and addresses the foregoing disadvantages, and others, of prior art eye patches. Accordingly, it is an object of the present invention to provide an improved eye patch for atraumatically immobilizing the lid of an eye.

It is a further object of the present invention to provide an improved patch that can immobilize the eyelid without damaging the eye from excessive pressure.

It is a further object of the present invention to provide an atraumatic self-adhering eye patch that can be easily applied by a patient or physician.

It is a further object of the present invention to provide an improved resilient eye pad for use with conventional adhesion devices.

It is another object of the present invention to provide an improved atraumatic eye patch that disperses the pressure necessary to maintain the eyelid immobilized about a larger area of the eyelid.

These and other objects are achieved by providing a self-adhering eye patch comprising an adhesive backing member for securing the patch to the face of a user. The eye patch also includes inner means for atraumatically maintaining the lid of the eye closed, the inner means including a foam member secured to the backing member and being configured to conform substantially to the shape of an eye socket, and a cover member covering at least the portion of the foam member that contacts skin. The inner means for maintaining the lid of the eye closed is of sufficient thickness to maintain the lid securely closed without damaging the eye.

These and other objects of the present invention are also achieved where the patch includes an absorbent pad member adjacent the foam member and the cover member surrounds the foam member and pad member, with the foam member being adhesively secured to the backing member.

Generally, the present invention also includes a self-adhering eye patch comprising a backing member for securing the patch to the face of a user, the backing member having an outer protective side and an inner adhesive side, with the inner adhesive side having adhesive on at least a sufficient portion of its circumference so that when applied to the face, it will provide adhesive force in all quadrants of the eye patch. In addition, the patch includes a resilient inner foam member for atraumatically maintaining the lid of the eye closed, the inner foam member being secured to the inner side of the backing member, the inner foam member being of sufficient thickness to maintain the lid securely closed wherein the resilient foam member is biased in all quadrants between the adhesive backing and face, thereby atraumatically maintaining the lid closed with minimal force.

In addition, the present invention also includes an eye pad comprising a layer of resilient foam material, the foam material being generally configured to the shape of an eye socket and sufficiently dimensioned to atraumatically maintain the eyelid closed when secured thereover. A covering associated with the foam layer is provided to prevent irritation of the lid and surrounding skin during use, wherein the eye pad is adapted to be placed over the eyelid and secured thereat to maintain the lid closed.

Further, the invention also includes a self-adhering eye patch comprising an adhesive backing member for securing the patch to the face of the user. The patch further includes inner means for atraumatically maintaining the lid of the eye closed, the inner means including a fluid filled bladder secured to the backing member and being configured to conform substantially to the shape of an eye socket. The inner means further including a cover member covering at least the portion of the fluid filled bladder that contacts skin, the inner means for maintaining the lid of an eye closed being of sufficient thickness to maintain the lid securely closed without damaging the eye. In addition, the fluid filled bladder may include means for adjusting the amount of fluid therein.

Some features and advantages of the present invention include easy ability to apply to the user by a doctor, or reapply by a user after use of eye drops or the like. In addition, the present invention maintains the eyelid securely closed without placing excessive pressure on or damaging the eye. Further, because the inner means is compressed when applied, and the adhesive backing maintains it in a compressed manner, the patch does not interfere with the wearing of eyeglasses.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Figure 1:
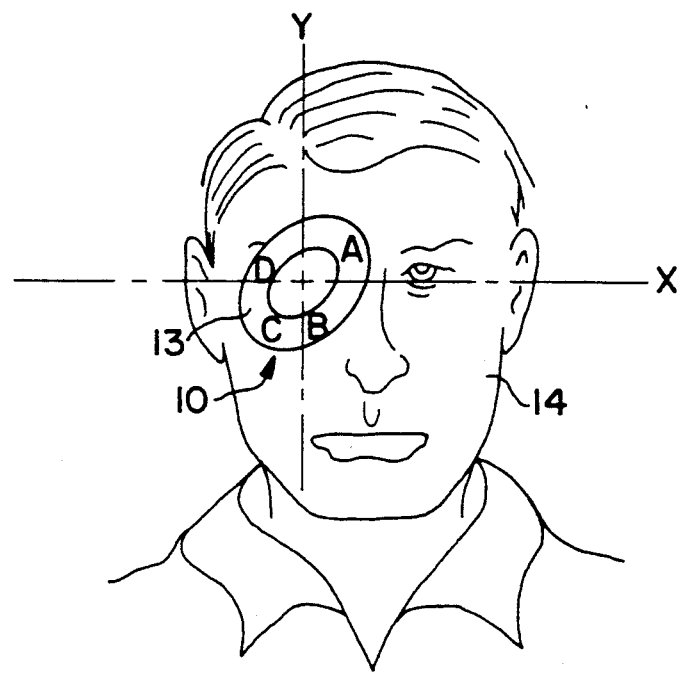
FIG. 1 is a perspective view of an eye patch in accordance with the present invention applied to the face of a user.

Repeat use of reference characters in the present specification and drawings is intended to represent same or analogous features or elements of the invention.

DETAILED DESCRIPTION OF PREFERRED EMBODIMENTS

Figure 2:
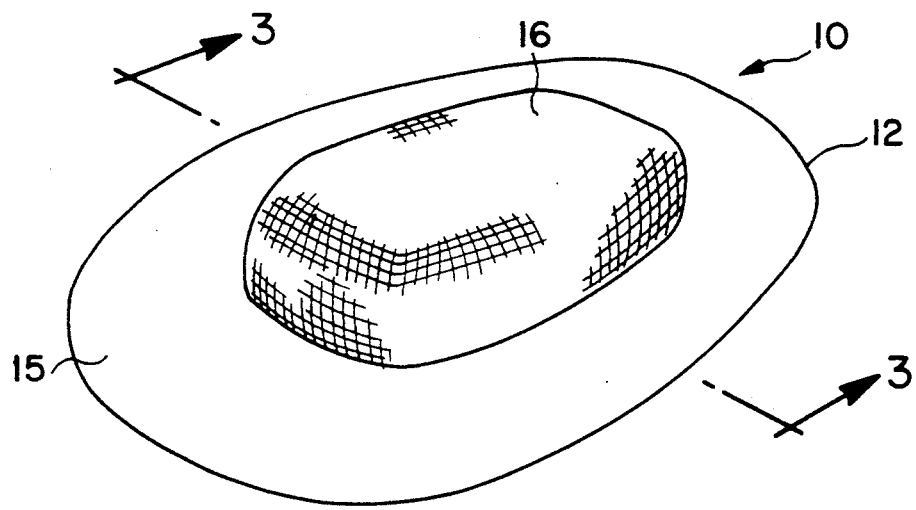
FIG. 2 is a perspective view of a preferred embodiment of an eye patch of the present invention.

It is to be understood by those of ordinary skill in the art that the present discussion is a description of exemplary embodiments only, and is not intended as limiting the broader aspects of the present invention, which broader aspects are embodied in the exemplary constructions. Referring to FIGS. 1 and 2, an eye patch in accordance with the present invention is generally illustrated as 10 and includes an adhesive backing member 12 for securing the patch to the face of a user 14. Adhesive backing member 12 includes an outer protective side 13 and an inner adhesive side 15. Adhesive backing member 12 can be adhesive about its entire inner side circumference, or may have intermittent non-adhesive portions. It is desirable, however, that sufficient adhesive be provided around the circumference of the eye patch to provide a substantially uniform force holding the eye patch in place. In this regard, the circumference of the patch can be defined as being located in four quadrants created by the intersection of an X and Y axis as illustrated in FIG. 1. The portion of the patch lying in each quadrant can be defined as A, B, C and D. It is important in the present invention that the patch be adhesive in at least a portion of each quadrant so that a substantially uniform compression of the foam will occur around the circumference of the patch when applied to the face of a user.

Adhesive backing 12 also includes a removable non-stick surface 22 (FIG. 3) for grasping the eye patch 10 prior to application, the non-stick surface adapted to be removed prior to applying the patch to the user.

Adhesive backing 12 is preferably a polyvinyl chloride film coated on one side with a non-sensitizing acrylic adhesive. One such product is MED 5502 Flesh Vinyl sold by Avery Specialty Tape Division of Painesville, Ohio. It should be understood, however, that any adhesive tape with sufficient adhesive qualities to maintain the patch in place could be used. For example, in an alternate embodiment, a stretchable adhesive tape such as that sold by Johnson & Johnson under the trademark ELASTIKON ™ could be used as the adhesive backing member. Such a tape is elastic and porous to allow the skin to breathe under the contact area. In addition, a material permeable to water vapor and air could also be used as well as a non-elastic porous material. It is also preferred that the adhesive backing be waterproof so that the patch can be worn during bathing and inclement weather.

Figure 3:
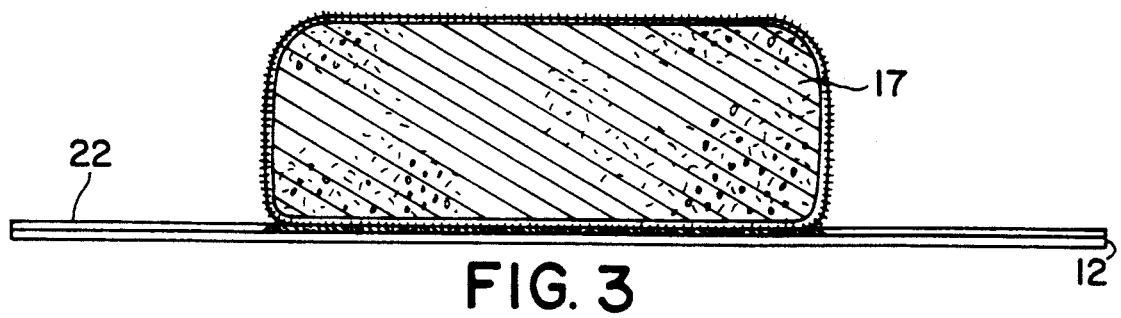
FIG. 3 is a cross-section taken along lines 3—3 of FIG. 2.
Figure 5:
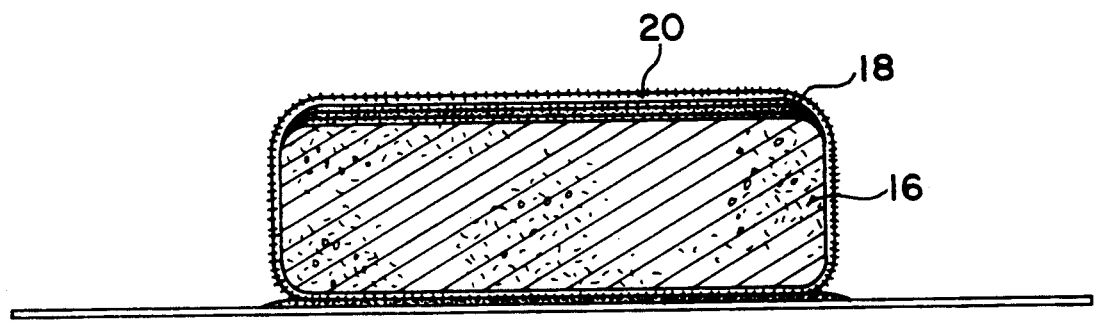
FIG. 5 is a cross-section of yet another preferred embodiment of the present invention.

As best illustrated in FIG. 2, the eye patch includes inner means for atraumatically maintaining the lid of the eye closed. As embodied herein and illustrated in FIGS. 2, 3 and 5, the inner means 16 includes a foam member 17 secured to the backing member 12. The foam member is configured to conform substantially to the shape of the eye socket of the user, said configuration being substantially oval in a preferred embodiment. However, any configuration that would maintain the lid closed could be utilized. As best illustrated in FIG. 5, the inner means 20 may include an absorbent pad member 18 adjacent the foam member 17 and a cover member 20 covering the absorbent pad 18 and the foam member 17. In a preferred embodiment, as illustrated in FIG. 3, the eye patch 10 may include a cover 20 over the foam member 17 and without the absorbent pad 18 illustrated in FIG. 5.

The absorbent pad member 18 is preferably a gauze type pad of cotton or other textile material to absorb drainage of the eye. However, any type absorbent material could be used for the pad. For example, a material permeable to water vapor and air would also be within the scope of the present invention. In addition, if so desired for a particular application, a non-absorbent pad could be used or a pad containing medication for treatment of the eye while patched. Further, the pad is preferably of a thickness less than that of the foam, and preferably less than one-half of the foam, but various relative thicknesses between the pad and foam have been found effective.

Cover member 20 is preferably a stretchable textile, but could be non-stretchable or of any non-textile material that would cover the pad 18 or foam 17 to prevent irritation of the contacted skin. In one embodiment, as illustrated in FIG. 5, cover member 20 surrounds pad member 18 and foam member 17 and is secured to the adhesive backing to hold the pad member and foam member in place. However, either pad member 18 or foam member 17 could be adhered directly to the adhesive backing. It is also possible for cover member 20 to be adhered to the inner foam member 17 such as by heat lamination. In such an embodiment, there would essentially be a padded cover. It would not be necessary in such an embodiment for the cover 20 to have sides 21 that extend over the edge of foam member 17. Further, if cover 20 or pad 18 is heat laminated to foam 17, the edges of the cover or pad and the foam could be thermally sealed to prevent exposure of the foam on its ends.

The inner means 16 for maintaining the lid of the eye closed is of sufficient thickness to maintain the lid securely closed without damaging the eye. That is, the inner means 16 should be of sufficient size and resilience to maintain the lid closed without producing excessive pressure on the eye when the patch is applied to a user. In this regard, it is preferable to use a resilient urethane foam with a density of 0.90±0.05 (pcf) and a resilience of 40–48 percent rebound. In addition, a most preferred embodiment of the present invention utilized a foam with an indention load deflection of less than 50 and preferably approximately 34. However, any foam with sufficient resiliency to maintain the lid closed without exerting excessive pressure on the eye could be used. It is currently preferred to use an open cell foam, but a closed cell foam with sufficient resilience could also be used.

In a preferred embodiment, the eye patch is approximately 8.5 cm long and 7 cm wide at its center. The inner means is preferably between approximately 1.25 cm and 1.5 cm thick. These dimensions are by example only and could vary without departing from the spirit of the invention as would be readily apparent to one skilled in the art. In addition, the relative thickness of the foam to the overall inner means can vary so long as sufficient thickness of foam is provided to maintain the resiliency of the inner means.

Figure 4:
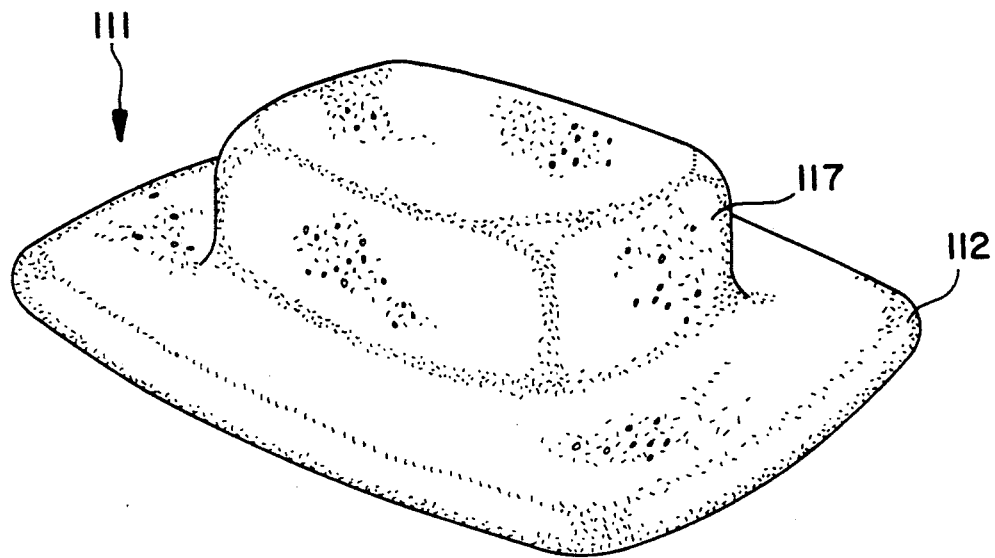
FIG. 4 is a perspective view of another preferred embodiment of the present invention.

In another preferred embodiment of the invention, as illustrated in FIG. 4, the eye patch comprises a resilient foam member 111 for atraumatically maintaining the lid of the eye closed. The foam member 111 has a first means adapted for biasing the lid and a second means for adhesively contacting the skin to maintain the patch in place.

As embodied herein, the first means adapted for biasing the lid comprises foam portion 117 that protrudes outwardly and is adapted to fit into the eye socket. As embodied herein, the second means for adhesively contacting the skin to maintain the patch in place comprises foam portion 112 that is integral and unitary with foam portion 117 providing a one piece foam member 111. Foam member 111 can be molded, die cut or produced in any other manner readily apparent to one skilled in the art. Portion 112 can be made adhesive by use of double-sided adhesive tape, impregnated with adhesive, or by any other means of providing portion 112 with an adhesive surface on its inside portion that will contact the skin when in use.

In the embodiment of FIG. 4, foam member 117 may include a cover member and/or a pad member as discussed above with respect to the embodiment of FIGS. 2, 3 and 5. The cover member and pad member may be secured to foam portion 116 by adhesive, laminated, or any other conventional means. As discussed above, foam portion 117, in combination with the pad member and cover member if used, must be of sufficient dimension and resiliency to atraumatically maintain the lid closed when applied to the face of a user.

In another preferred embodiment of the present invention, the inner means can include a detached pad as shown at 16 in FIG. 2 but detached from any adhesive backing. This pad can be utilized in combination with the embodiments set forth in FIGS. 1–7. Such an additional detached pad, comprising a foam number 17 and a cover member 20, could be utilized to adapt the eye patch 10 of the present invention to eye sockets deeper than normal. The detached pad can be placed in the eye socket, and the patch 10 placed thereover to provide a thicker inner means, while still maintaining sufficient resiliency to atraumatically maintain the lid closed. The detached pad can also include an absorbent pad therein, such as 18, as disclosed with regard to the inner means 16 in FIG. 5.

In another preferred embodiment, the inner means 16 could be utilized as an eye pad without adhesive backing. Such a pad could be secured to the user with conventional means such as tape or the like and should be dimensioned to atraumatically maintain the eyelid closed when secured to the face of a user. Appropriate dimensions and characteristics would be as set forth above.

The inventor has conducted tests utilizing the invention as embodied in FIGS. 2 and 5. The tests were performed by placing a polyethylene vessel between the inner means 16 and the eyelid and securing the patch to the face of the test subjects. An arterial pressure transducer was connected to the vessel and to a digital manometer having a sensitivity of 1 mm of mercury. Pressures were recorded in the vessel by means of an intravesicular needle connected to the pressure transducer. Random subjects were selected and patched using the device. Pressure generated within the vessel was believed to represent the force applied to the lid of the eye by the patch. Eleven subjects were tested with resultant pressures ranging from 5 to 13 mm of mercury.

Based on these tests and subjective comfort tests, it would appear that the patch of the present invention maintains the lid of the user closed with a minimal amount of pressure on the lid, and therefore, on the eye. It is thought that this results from the combination of use of a resilient member, such as the foam, in combination with the adhesive means, secured to the face in at least a portion of all four quadrants. This provides a uniformly disbursed pressure on the lid that is spread about the circumference of the eye, therefore minimizing locations of high pressure that are produced by patches secured with straps (2 points of pressure where strap attaches to backing) and adhesive patches that do not contain a resilient member (where the portion contacting the lid cannot uniformly distribute the forces).

Figure 6:
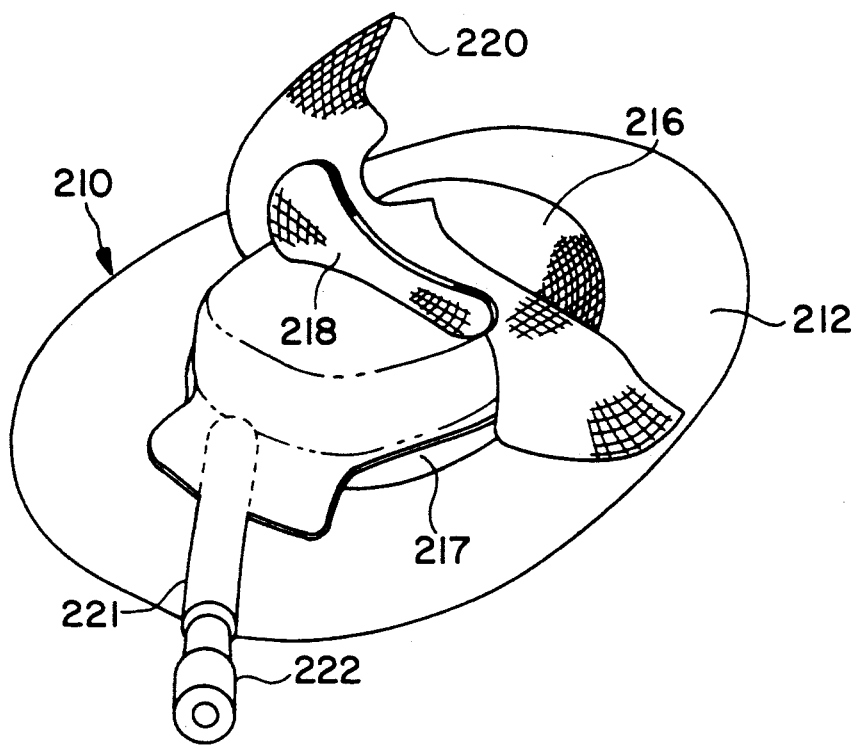
FIG. 6 is a perspective view of an eye patch in accordance with another embodiment of the present invention.
Figure 7:
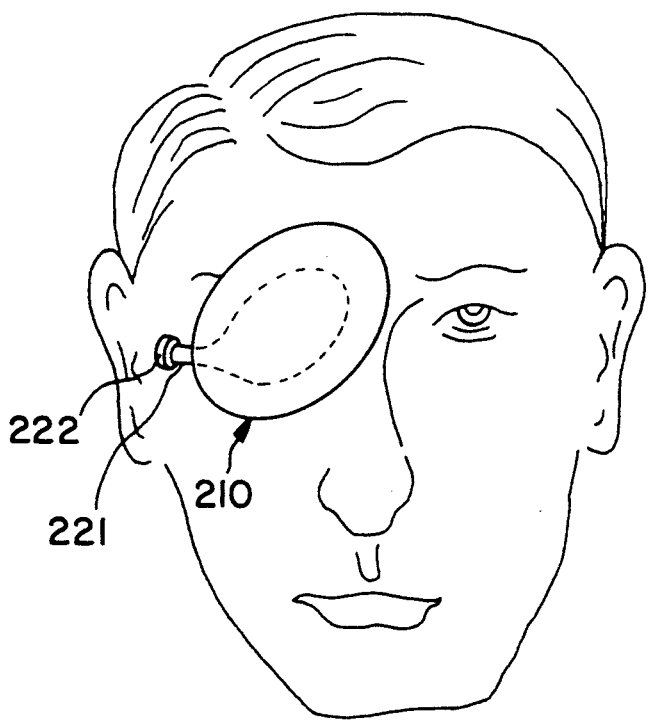
FIG. 7 is a perspective view of the embodiment of FIG. 6 in place on the face of a user.

Another preferred embodiment of the present invention is illustrated in FIGS. 6 and 7 at 210. Eye patch 210 includes inner means 216. As embodied herein, inner means 216 comprises a fluid filled bladder 217. Preferably, fluid filled bladder 217 is inflatable.

Inner means 216 may be secured to adhesive backing 212 by any conventional means. In addition, inner means 216 may also include a cover member 220 and a pad member 218. Either cover member 220 or pad member 218 can be used in combination or by themselves with bladder 217. Cover member 220 and pad member 218 may be as described above with respect to the embodiments of FIGS. 1–5. In addition, the eye patch of this embodiment could be utilized without cover member 220 or pad 218.

As illustrated in FIGS. 6 and 7, bladder 217 includes inlet portion 221 with connector means 222. Air or other fluid can be introduced into bladder 217 to adjust the pressure applied to the lid when the patch 210 is in place. As illustrated in FIG. 7, when eye patch 210 is in place, inlet portion 217 and connector means 222 extend to a position so that the pressure in bladder 217 can be adjusted while the patch is in place. Pressure in bladder 217 can be increased or reduced through connector means 222 by any conventional means such as an air pump, or a syringe. Connector means 222 serves as a valve means maintaining the pressure in inflatable bladder 217 until such pressure is released.

The characteristics of backing 212 are as set forth in the above embodiments with regard to backing 12. For example, it is desirable for backing 212 to be adhesive in at least a portion of each quadrant as illustrated in FIG. 1.

As utilized herein, fluid includes any type gas or liquid capable of maintaining bladder 217 inflated. Further, bladder 217 is preferably constructed of a polymeric material that is adapted to expand to a generally predetermined configuration as illustrated in FIG. 6. Of course, any type material that could be inflated to a substantially predetermined shape or configuration would be suitable. In addition, bladder 217 may include baffles therein to provide more uniform movement of the fluid therein and more uniform pressure exerted when the bladder is inflated, deflated or applied to the eyelid.

As to the embodiments of FIGS. 1–7, the adhesive layer could alternately comprise a hook and loop arrangement where one of the hook or loop side could be adhesively secured to the user's face and the other of the hook or loop side secured to the backing. The patch could then be repeatedly applied to the user without removing the adhesively attached portion from the user's face. In addition, it is preferable that the eye patch of the present invention be sterile.

As best illustrated in FIG. 1, it is preferred that the patch of the present invention be applied in an offset manner as illustrated. This provides for better adhesive to the face of a user. In addition, it is preferred that the patch be applied by placing it in the palm of a hand and compressing the inner means into the eye socket with the palm. Such secures the patch to the face with the inner means at least partially compressed.

These and other modifications and variations to the present invention may be practiced by those of ordinary skill in the art, without departing from the spirit and scope of the present invention, which is more particularly set forth in the appended claims. Furthermore, those of ordinary skill in the art will appreciate that the foregoing description is by way of example only, and is not intended to be limitative of the invention so further described in such appended claims.

What is claimed is:

1. A self-adhering eye patch, said eye patch comprising:
   an adhesive backing member for securing the patch to the face of a user; and
   inner means for atraumatically maintaining the lid of the eye closed, said inner means including a foam member secured to said backing member and being configured to conform substantially to the shape of an eye socket, and a cover member surrounding said foam member so as to cover the entire portion of said foam member that contacts skin, said inner means for maintaining the lid of an eye closed being of sufficient thickness to maintain the lid securely closed without damaging the eye.

2. A self-adhering eye patch as in claim 1, wherein said foam member is adhesively secured to said backing member.

3. A self-adhering eye patch as in claim 1, wherein said cover member is a stretchable material.

4. A self-adhering eye patch as in claim 1, wherein said adhesive backing is a stretchable material.

5. A self-adhering eye patch as in claim 1, wherein said adhesive backing includes a removable non-adhesive peripheral portion for grasping prior to application.

6. A self-adhering eye patch as in claim 1, wherein said eye patch is sterile to prevent contamination of the eye.

7. A self-adhering eye patch, said eye patch comprising:
   a backing member for securing the patch to the face of a user, said backing member having an outer protective side and an inner adhesive side, said inner side having adhesive on at least a sufficient portion of its circumference so that when applied to the face it will provide adhesive force in all quadrants of the eye patch;

a resilient inner foam member for atraumatically maintaining the lid of the eye closed, said inner foam member being secured to the inner side of said backing member, said inner foam member being of sufficient thickness to maintain the lid securely closed, wherein the resilient foam member is biased in at least a portion of all quadrants between the adhesive backing and face thereby atraumatically maintaining the lid closed; and further comprising a cover member surrounding said foam member so as to cover the entire portion of said foam member that contacts skin.

8. A self-adhering eye patch as in claim 7, wherein said adhesive backing member is a stretchable material.

9. A self-adhering eye patch as in claim 7, wherein said eye patch is sterile to prevent contamination of the eye.

10. An eye pad adapted to be secured over the lid of an eye, said eye pad comprising:

a layer of resilient foam material, said foam material being generally configured to the shape of an eye socket and sufficiently dimensioned to atraumatically maintain the eyelid closed when secured thereover; and a covering surrounding said foam layer to prevent irritation of the lid and surrounding skin during use, wherein said eye pad is adapted to be placed over the eyelid and secured thereat to maintain the lid closed.

11. An eye pad as in claim 10, wherein said covering comprises a stretchable material that expands and contracts with the foam material as it is compressed or released.

* * * * *